United States Patent [19]

Berg

[11] Patent Number: 4,582,994

[45] Date of Patent: Apr. 15, 1986

[54] GAMMA CAMERA

[75] Inventor: Jan Berg, Virum, Denmark

[73] Assignee: General Electric Company, Milwaukee, Wis.

[21] Appl. No.: 554,401

[22] Filed: Nov. 23, 1983

[30] Foreign Application Priority Data

Jul. 5, 1983 [DK] Denmark .............................. 3115/83

[51] Int. Cl.[4] ............................................ G01T 1/202
[52] U.S. Cl. ............................... 250/363 S; 250/515.1
[58] Field of Search ............. 250/363 S, 505.1, 515.1; 378/145, 147

[56] References Cited

U.S. PATENT DOCUMENTS 3,883,742  5/1975  Olson et al. ...................... 250/515.1
3,982,133  9/1976  Jupa et al. ........................ 250/363 S
3,986,036 10/1976  Harper et al. .................... 250/515.1
3,995,163 11/1976  Colditz ............................. 250/515.1

Primary Examiner—Alfred E. Smith
Assistant Examiner—Richard Hanig
Attorney, Agent, or Firm—Douglas E. Stoner; Alexander M. Gerasimow

[57] ABSTRACT

In a gamma camera at least a part of an outer shell of lead and preferably also of the inner casing of steel surrounding a scintillation crystal is cut away on one side and is replaced with a flat but thinner plate of a material having better radiation absorbing characteristics, such as tungsten. In this way, the distance from the outside edge to the useful central measuring area is reduced on that side such that the camera can be rotated in the smallest possible circle around the head of a patient to perform a more complete and precise measurement on the majority of the head.

10 Claims, 2 Drawing Figures

GAMMA CAMERA

BACKGROUND OF THE INVENTION

The present invention relates generally to scintillation cameras and more particularly to a gamma camera having a radiation absorbing shell of lead, a casing of steel surrounding a scintillation crystal, a plurality of photomultiplier tubes and a collimator.

In the use of a gamma camera for performing tomography, it is important for good resolution that the distance between the camera and the patient is a minimum. Since it is desirable to have the camera field of view centered as close as possible to the area of interest in the head, when a conventional gamma camera is applied to brain tomography, it may be necessary that the camera be entirely outside the patient's shoulders, when it is rotated around the patient. A displacement of the camera upwards from the patient's shoulders so that the camera could be rotated close to the head of the patient would result in only the very topmost part of the head being examined. This is due to the fact that around the central measuring part of the camera there is a border zone which cannot produce exact data, and furthermore, around this border zone there is a thick shell of lead.

The object of the present invention is to improve a gamma camera so that it is not only useful for ordinary tomography, but it is also particularly suitable for brain tomography. According to the invention, this is accomplished by cutting away at least the part of the shell of lead on the side of the camera nearest to the patient and covering that side with a plate of a material with a high radiation absorption capability, such as tungsten. In a particularly advantageous embodiment of the invention, a part of the casing of steel surrounding the scintillation crystal is also cut away.

By this structural change, the distance from the most useful central part of the camera to a physical outer side thereof is reduced sufficiently that the camera can be rotated in the smallest possible circle around the head of the patient while still covering substantially all of the head, so that brain tomography can be performed with maximum quality. Moreover, this is obtained without detracting from the general applicability of the camera for performing tomography. This reduction of the distance of the useful central part of the camera from the outer side thereof is of course greatest in case of a circular camera but is also applicable with other shapes of the camera. The reduction of the distance is obtained by cutting away the thick shell of lead and replacing it by a thinner type of absorbing plate, e.g., tungsten, making sure that the shielding then takes up a minimum of space. When a part of the crystal casing of steel is also cut away, admittedly, a part of the outer border zone surrounding the central detecting zone of the camera is removed, but this will have no adverse affect on the central active zone. Because of the high prices on tungsten and other well-shielding materials, an economic advantage is obtained by providing such materials at only the part of the shielding nearest to the patient while the rest of the shell of lead remains. For aesthetic reasons, however, the entire chordal portion associated with the shell of lead may be cut away and replaced with a plate of tungsten. It is also possible to remove only the lower portion of the camera nearest the patient and to leave the leaded upper part of the shielding remote from the patient, as the upper part of the camera, containing among other things electronic equipment, allows the required reduction of this compartment which is necessitated by the thicker shielding of lead.

BRIEF DESCRIPTION OF THE DRAWINGS

The features of the invention believed to be novel are set forth with particularity in the appended claims. The invention itself, however, both as to its organization and method of operation, together with further objects and advantages thereof, may best be understood by reference to the following description taken in conjunction with the accompanying drawings in which:

DETAILED DESCRIPTION OF THE PREFERRED EMBODIMENT

Figure 1:
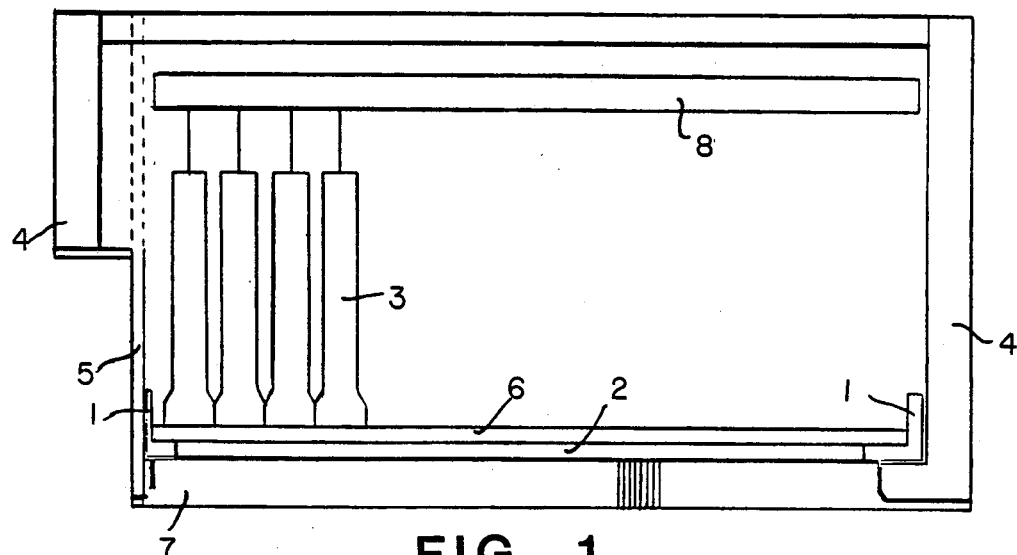
FIG. 1 shows a schematic frontal view of an embodiment of a gamma camera according to the invention, and FIG. 2 the same seen in a plan view from below in FIG. 1.
Figure 2:
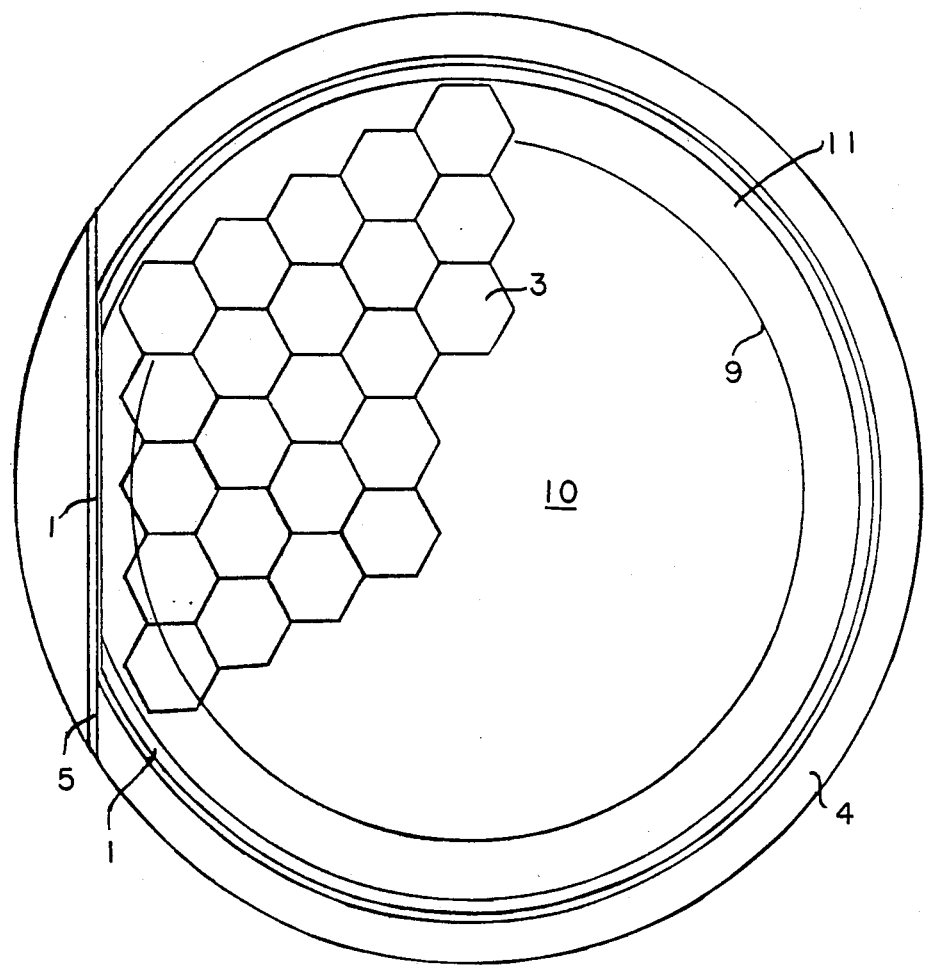

In FIGS. 1 and 2, a camera is shown to include a casing of steel 1 surrounding a scintillation crystal 2, which is covered by a glass sheet 6 over which there are provided a plurality of photomultiplier tubes 3 of which only some are shown. Under the crystal 2 a collimator 7 is provided in the usual way. For the prevention of interfering entrance of radiation from the sides, the camera is provided with a heavy surrounding shell 4, which for price reasons is usually made of lead.

In FIG. 2 a circle 9 is shown inside which the usable measuring area 10 is to be found. In a border zone 11 outside the circle 9 exact measuring values cannot be obtained in sufficient volume to make it very useful.

For reducing the distance from the physical outer edge of the camera to the area 10, a part of the shell of lead 4 and of the casing of steel 1 is cut away on one side of the camera as is clearly shown. Also removed is a part of the border zone 11 but without detracting from the performance of the camera in that area. As is apparent from FIG. 1 only the part of the shell of lead 4 and of the casing of shell 1, nearest the patient, is removed while the remote upper part of the shell of lead is retained for strength reasons. In a practical embodiment the shell of lead was cut away at a distance of approximately 17 cm from the side of the camera facing the patient whereby the camera may be moved in a small circle around the head of the patient and still be clear of the shoulders of the vast majority of patients. As shown in FIGS. 1 and 2 the radiation shielding in the cutout section is provided by means of a relatively thin flat plate 5 which consists of a material with a high absorption capability for providing sufficient radiation absorption. To this end tungsten is particularly suitable, but other heavy materials could theoretically also be useful, e.g., gold or uranium.

The plate 5 may, for example, be glued in place or fastened with screws.

In FIG. 1 an extension of the plate 5 through the camera to its upper side is shown with dotted lines. This may in some cases be desirable, among other things, for the sake of the appearance, but as a further possibility the shell of lead 4 on the upper part of the camera may be located flush with the plate 5, as the electronics 8 placed in the upper part of the camera can easily be packed together to leave space for the thicker shielding of lead at this location. Because of a very high price on tungsten, such an embodiment may be desirable.

While this invention has been described with reference to particular embodiments and examples, other modifications and variations will occur to those skilled in the art in view of the above teachings. Accordingly, it should be understood that within the scope of the appended claims the invention may be practiced otherwise than is specifically described.

What is claimed is:

1. A gamma camera having a radiation absorbing shell of lead, a casing of steel, a scintillation crystal, a plurality of photomultiplier tubes, and a collimator, wherein at least a portion of the shell of lead is cut away on one side with that side being covered with a shield of a material having a higher radiation absorption capability than lead to thereby reduce the distance from the center of the camera to its outer side at the position of said shield.

2. A gamma camera according to claim 1, wherein a portion of the casing of steel is also cut away.

3. A gamma camera according to claim 1 or 2, wherein on said one side of the camera the entire thickness of said shell of lead is cut away and covered by said shield of a material with a higher radiation absorption capability.

4. A gamma camera according to claim 1 or 2, wherein the outside of the shell of lead on the said side of the camera is flush with said shield of a material with a higher radiation absorption capability.

5. An improved gamma camera of the type having a lead shield surrounding both a scintillation crystal and a plurality of photomultiplier tubes longitudinally disposed in close proximity to the scintillation crystal, wherein at least a portion of the lead shield is discontinuous and the discontinuity is bridged with a thinner protective plate having greater X-ray absorption characteristics than lead, to thereby reduce the distance from the center of the camera to its outer side at the position of the protective plate.

6. An improved gamma camera as set forth in claim 5 wherein said protective plate is composed of a tungsten material.

7. An improved gamma camera as set forth in claim 5 wherein said protective plate is planar in form.

8. An improved gamma camera as set forth in claim 5 wherein said discontinued portion includes only a lower longitudinal portion at the end of the camera containing the scintillation crystal and does not include the corresponding upper portion thereof.

9. An improved gamma camera as set forth in claim 8 wherein said protective plate extends longitudinally upward, beyond the location from which said lower longitudinal portion is discontinued, and internal to said corresponding upper portion.

10. An improved gamma camera as set forth in claim 5 wherein the camera also includes a steel casing disposed between the scintillation crystal and lead shield and further wherein a portion of the steel casing is discontinuous.

* * * * *